United States Patent [19]

Stanec

[11] Patent Number: 4,982,744

[45] Date of Patent: Jan. 8, 1991

[54] HAND AND ARM BOARD FOR USE IN INTRAVENOUS ADMINISTRATION AND OTHER MONITORING TESTS

[76] Inventor: George Stanec, 15 Secor Rd., Scarsdale, N.Y. 10583

[21] Appl. No.: 257,581

[22] Filed: Oct. 14, 1988

[51] Int. Cl.⁵ ............................................. A61F 5/00
[52] U.S. Cl. .................... 128/877; 128/879; 128/DIG. 6; 128/DIG. 15
[58] Field of Search ............... 128/877, 878, 879, 894, 128/77, 84 R, 84 C, DIG. 15, DIG. 6; 604/179, 180

[56] References Cited

U.S. PATENT DOCUMENTS

| | | | |
|---|---|---|---|
| 2,763,264 | 9/1956 | McInnerney | 128/877 |
| 2,998,008 | 8/1961 | Klesa | 128/878 |
| 3,059,636 | 10/1962 | Schwartz | 128/877 |
| 3,086,529 | 4/1963 | Munz | 128/DIG. 15 |
| 3,196,870 | 7/1965 | Sprecher | 128/877 |
| 3,295,518 | 1/1967 | Hazlewood | 128/877 |
| 3,480,013 | 11/1969 | Garber | 128/877 |
| 3,556,092 | 1/1971 | Eisenberg | 128/877 |
| 3,640,273 | 2/1972 | Ray | 128/877 |
| 3,788,307 | 1/1974 | Kistner | 128/77 |
| 3,789,842 | 2/1974 | Froinson | 128/DIG. 15 |
| 3,866,611 | 2/1975 | Baumrucker | 128/DIG. 15 |
| 3,896,799 | 7/1975 | Seeley | 128/877 |
| 4,122,857 | 10/1978 | Haerr | 604/108 |
| 4,286,588 | 9/1981 | Louegrove | 128/877 |
| 4,425,913 | 1/1984 | Lewis | 128/872 |
| 4,457,754 | 7/1984 | Buttaravoli | 128/877 |
| 4,489,716 | 12/1984 | Blackwood | 128/77 |
| 4,503,849 | 3/1985 | Morgan et al. | 128/877 |
| 4,531,942 | 7/1985 | Turner | 604/180 |
| 4,591,148 | 5/1986 | Slater | 128/DIG. 15 |
| 4,615,046 | 10/1986 | Martin | 128/77 |
| 4,628,917 | 12/1986 | Campagna Jr. et al. | 128/90 |
| 4,633,863 | 1/1987 | Filips | 128/877 |
| 4,678,462 | 7/1987 | Vailancourt | 128/877 |
| 4,738,662 | 4/1988 | Kalt | 128/DIG. 15 |

*Primary Examiner*—Robert A. Hafer
*Assistant Examiner*—Michael Brown
*Attorney, Agent, or Firm*—Sughrue, Mion, Zinn, MacPeak & Seas

[57] ABSTRACT

A device and method for immobilizing a patient's hand and/or forearm includes a composite sheet and an armboard. The composite sheet includes an adhesive surface on one side thereof and a fabric loop fastener on the other side. the armboard includes a fabric hook fastener on a side thereof. The patient's hand and/or forearm is secured to the composite sheet by placing the hand and/or forearm on the adhesive surface thereof. After the hand and/or forearm is secured to the composite sheet, the composite sheet is attached to the armboard by securing the fabric loop fastener of the composite sheet to the fabric hook fastener of the armboard. In this manner, the hand and/or forearm can easily be immobilized.

13 Claims, 4 Drawing Sheets

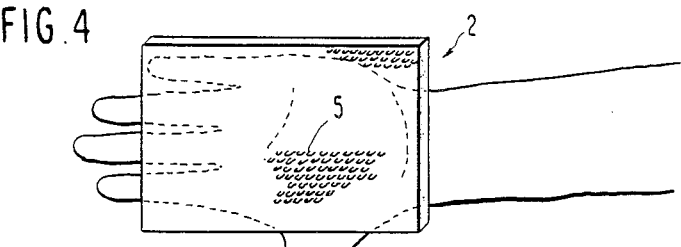
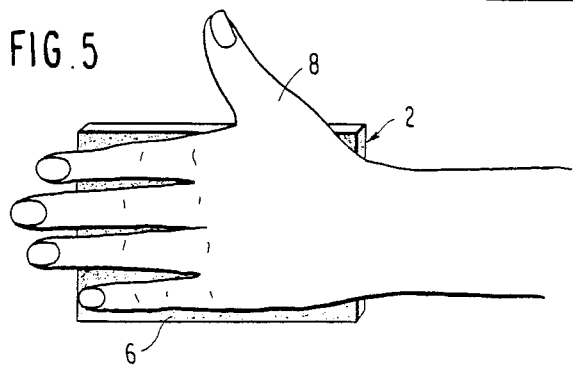
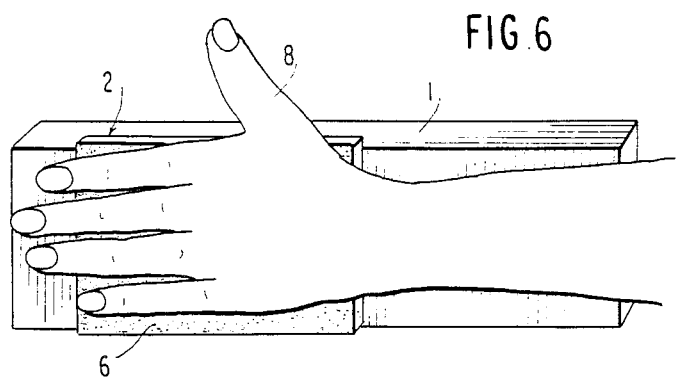
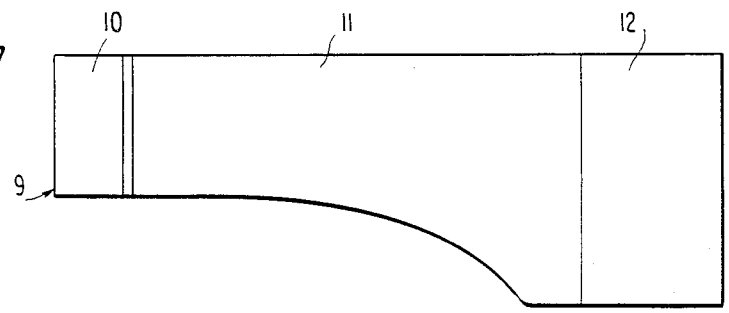
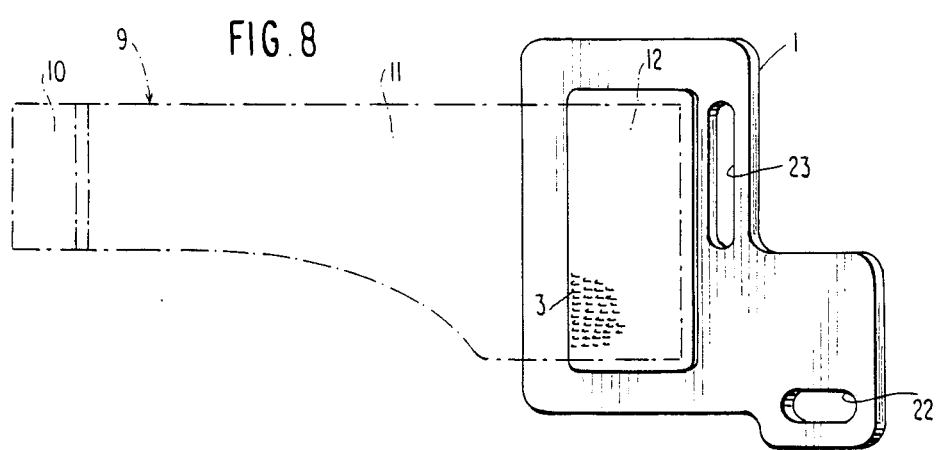

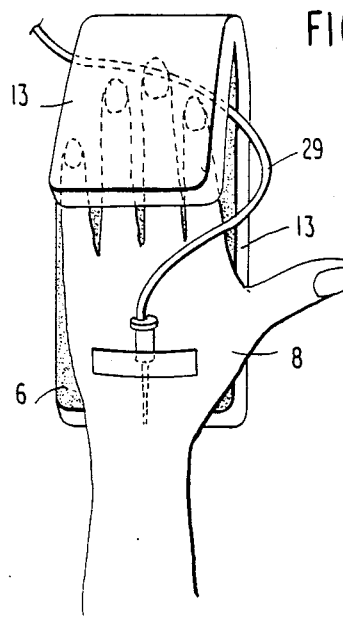
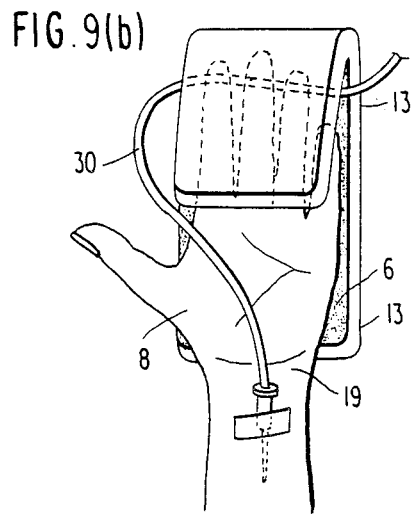
FIG.9(a)    FIG.9(b)
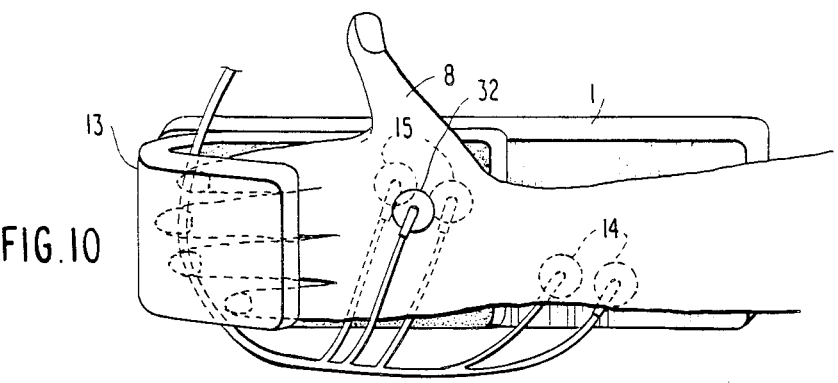
FIG.10
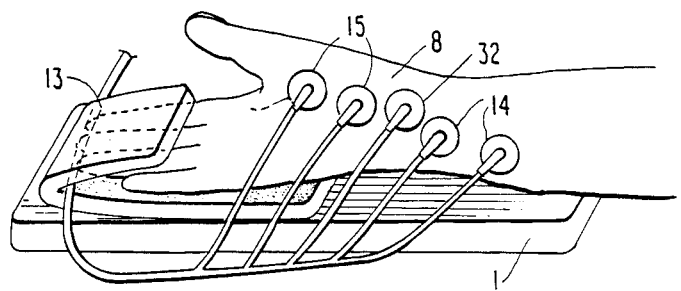
FIG.11(a)
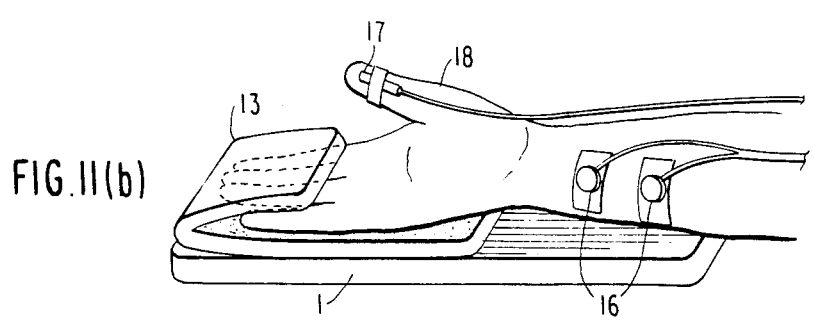
FIG.11(b)

4,982,744

HAND AND ARM BOARD FOR USE IN INTRAVENOUS ADMINISTRATION AND OTHER MONITORING TESTS

BACKGROUND OF THE INVENTION

The present invention is directed to a device and a method for using the same, for immobilizing a patient's hand and/or forearm by holding the hand and/or forearm securely to a board in order to facilitate intravenous administration of fluids, and to assist in conducting a variety of other monitoring tests.

The human hand is the site of a multiplicity of procedures carried out both during and after surgical procedures, and during other medical treatments. analyses, examinations, etc. Examples of some of the different procedures carried out which involve a person's hand and/or forearm are: intravenous fluid and blood administration, blood pressure monitoring. pulse oximetry, neuromuscular function monitoring by force or acceleration measurements, etc. In spite of this fact, adequate systems have not heretofore been available for simple, but reliable immobilization of the hand and/or forearm. The present invention makes such immobilization possible, while allowing for quick adjustment of the hand for use with any number of various clinical monitoring tests and devices.

A number of restraints used to support and restrain a patient's hand and/or forearm for intravenous administration are known in the art. For example, U.S. Pat. Nos. 4.503,849; 4.425.913; 3,640,273; and 4.268.588 each disclose devices which temporarily restrain and support the hand and/or forearm using straps to secure the device thereto. However, the use of straps is disadvantageous in that the straps are difficult to secure and limit accessibility to the patient's hand and/or forearm.

U.S. Pat. Nos. 4,122,857 and 4,531,942 disclose devices for securing intravenous tubing, or the like, to a patient. However, neither of these devices includes a means for restraining a patient's hand or forearm.

Finally. U.S. Pat. No. 4,628,917 discloses a splint for immobilizing a patient's arm. However, the splint is secured to the patient's arm with a wrapping bandage. Accordingly, a device for securing a patient's hand and/or forearm which is secure and yet easily removable, has heretofore not been designed.

SUMMARY OF THE INVENTION

In the present invention, the armboard allows for a patient's hand and/or forearm to be comfortably and securely restrained. In addition, according to the present invention, the patient's hand and/or forearm can be easily removed and reattached to different armboards in various locations in a hospital or other health care facility, such as the operating room, recovery room, or intensive care unit.

Furthermore, the armboard, to which the patient's hand is secured, may have multiple uses. For instance, the armboard may contain a plurality of openings for securing a force transducer positioner or the like thereto. As such, the armboard of the present invention has various uses with a number of monitoring devices including an acceleration transducer, a force transducer, a pulse oximeter sensor and an intravenous cannula on the same hand and/or forearm.

An object of the present invention is to provide a means for securing a patient's hand and/or forearm in a secure and releasable manner, in order to immobilize the hand and/or forearm for use in intravenous administration of fluids, such as blood or plasma and to facilitate conducting various monitoring tests.

The present invention accomplishes these objectives through the use of a board having a fabric hook fastener bound to at least one side thereof and a composite sheet having an adhesive surface on one side thereof and a fabric loop fastener on the opposing side thereof. The patient's hand is secured to the composite sheet by means of the adhesive surface. Thereafter the composite sheet is secured to the board by connecting the fabric hook fastener of the board to the fabric loop fastener of the composite sheet.

BRIEF DESCRIPTION OF THE DRAWINGS

FIG. 4 is a bottom view of the attachment of the palmar side of the hand to the composite sheet;

FIG. 5 is a top view of the attachment of the of the palmar side of the hand to the composite sheet;

FIG. 6 is a top view showing the palmar side of the hand, with the composite sheet in place, attached to the armboard;

FIG. 7 is a plan view of the handbelt for use in the present invention;

FIG. 8 is a plan view of the handbelt and handboard employable in the present invention according to a second embodiment of the invention;

FIG. 9(a) is a plan view of the attachment of the palmar side of the hand to the extended composite sheet according to a further embodiment of the invention;

FIG. 9(b) is a bottom view of the attachment of the extended composite sheet to the dorsal side of the hand;

FIGS. 10 and 11(a), (b) and (c) are perspective views of the use of the present invention, employing the extended composite sheet, with various monitoring devices;

DETAILED DESCRIPTION OF THE INVENTION

Figure 1:
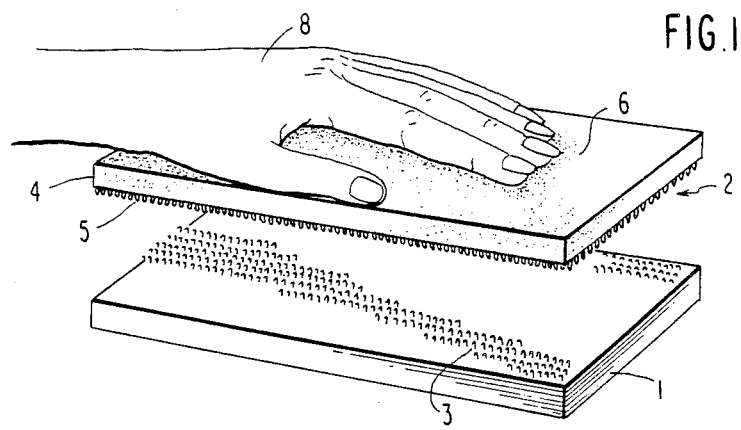
FIG. 1 is a perspective view showing the immobilization of a patient's hand according to the present invention.
Figure 2:
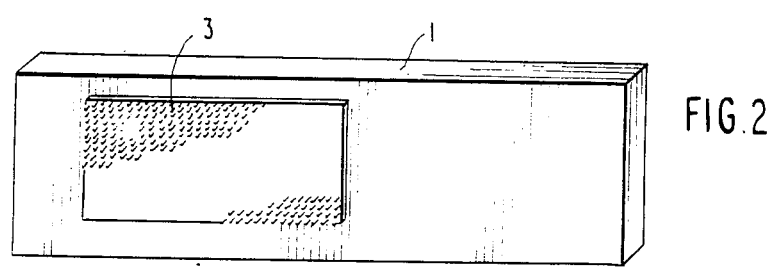
FIG. 2 is a perspective view showing the armboard with the fabric hook fastener bound thereon.

Referring to FIG. 1, the armboard device of the subject invention includes an armboard 1 and a composite sheet 2 for securing the hand and/or forearm to the armboard. As represented by FIGS. 1 and 2, the armboard 1 is of lightweight rigid construction and may be made from a lightweight plastic material or any other suitable material known in the art; A fabric hook fastener 3 is bound thereon by an adhesive FIG. 2 also shows the armboard with the straight rectangular shape particularly useful for intravenous administration. However, the size and shape of the armboard may vary according to the specific application of the present invention. Different sized armboards are useful for various age groups.

Figure 3A:
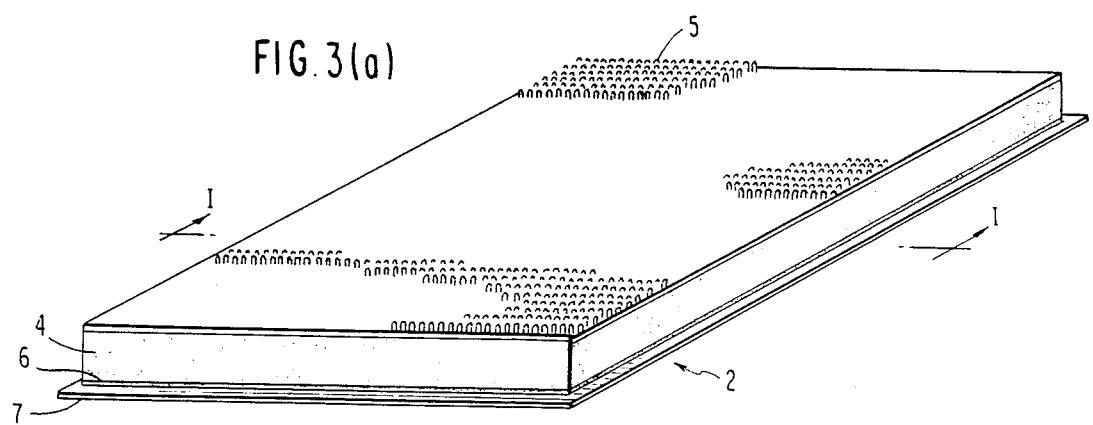
FIG. 3(a) is a perspective view showing the composite sheet employable in the present invention.
Figure 3B:
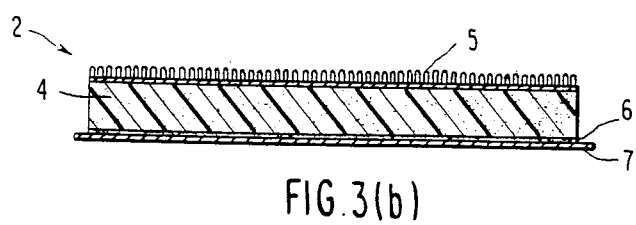
FIG. 3(b) is a cross-sectional view of the composite sheet taken along the line I—I in FIG. 3(a)

The composite sheet 2 may be attached to the armboard as shown in FIGS. 1 and 3(a). The composite sheet includes a breathable foam base 4 with a fabric loop fastener 5 adheredly secured on one side thereof and a pressure sensitive adhesive element 6, which may further be protected by release paper 7, on the other side. A cross-sectional view of the composite sheet is shown in FIG. 3(b). The pressure sensitive adhesive element of the present invention is approved for contact with the skin.

As is apparent from the above description and as illustrated FIGS. 3 and 4 the hand 8 (in palmar view in FIG. 4 and in dorsal view in FIG. 5) is attached to the composite sheet 2 with release paper 7 already removed. The composite sheet 2 may be attached to the palm or the back of the hand via the adhesive element 6, as required for a specific application. The fabric loop fastener 5, which is bound to the opposite side of the composite sheet, is adhesively attached to the fabric hook fastener 3 on the armboard 1, as shown in FIG. 6. The position of the fabric hook fastener and the fabric loop fastener 5 may be reversed (i.e., the fabric hook fastener may be bound to the composite sheet and the fabric loop fastener may be bound to the board). as required for a specific application of the present invention. The hand with the composite sheet in place becomes a single entity which can be easily removed and reattached to different armboards in various locations in the hospital, such as the operating room, recovery room, intensive care unit, etc.

FIG. 6 shows the correct immobilization of the hand in accordance with the present invention. The hand is immobilized on the armboard 1 with the composite sheet 2 interfacing with the fabric hook fastener 3 (not shown) on the board, thus forming a secure fabric loop/hook system with the fabric loop fastener 5 on the composite sheet 2. The hand, with the composite sheet in place, may alternatively be removed from the armboard and further secured to another armboard in other locations in the hospital.

FIG. 1 is a perspective view showing the correct immobilization of the hand with the present invention. The composite sheet 2 is attached to the hand 8 via the adhesive element 6. The fabric loop fastener 5 of the composite sheet 2, is securely and releasably immobilized on the board 1 via the fabric loop/hook connection formed with the fabric hook fastener 3 bound to the board.

According to another embodiment of the invention, the composite sheet 2 can include adhesive elements disposed on opposing sides of the foam base 4. For instance referring to FIG. 3(a) reference numeral 5 can represent an adhesive element in opposition to the adhesive element 6 formed on the foam base 4. Thus, after the patient's hand is secured to one side of the composite sheet via adhesive element 6, the composite sheet 2 can be adhesively secured to a rigid member via the opposing adhesive element 5.

The armboard of the present invention may further contain an opening for a handbelt 9. The handbelt 9 is wrapped around the hand which is in place on the armboard, thus forming a secure loop/hook connection in order to further immobilize the hand. Furthermore, the handbelt is particularly useful for keeping the hand warm during prolonged monitoring.

The handbelt may be manufactured from hook tape or any other applicable material. The handbelt 9 comprises a fabric hook fastener 10 and a fabric loop fastener 11 disposed on opposing sides thereof. FIG. 7 shows the handbelt, which attaches to the armboard via a loop/hook connection between the fabric loop fastener 11 of the handbelt 9 and the fabric hook fastener 3 bound to the board 1. As can be seen in FIGS. 7 and 8, the fabric loop fastener area 12 on the handbelt 9, is engaged with the fabric hook fastener 3 on the side of the armboard 1 opposite to the hand thus forming a secure loop/hook connection. The hand with the composite sheet in place, is placed on the board, and the handbelt 9 is wrapped around the hand and is pulled through the opening 23 on the armboard to form a secure loop/hook fastening system between the fabric loop fastener 11 and the fabric hook fastener 10.

In a further embodiment of the present invention, as shown in FIGS. 9(a) and g(b). the composite sheet may be extended in order to further immobilize the hand and secure intravenous or intra-arterial blood pressure tubing. FIG. 9(a) shows the dorsal side of the hand 8 with the extended composite sheet 13 attached to the palm and folded over the fingers of the hand and intravenous tubing 29. FIG. 9(b) shows the palmar side of the hand with the extended adhesive attached to the back of the hand B and folded over the fingers and intra-arterial blood pressure tubing 30 allowing for additional uses in a clinical setting.

The use of the extended composite sheet is further described with reference to FIGS. 10 (dorsal view) and 11(a)–(c) (palmar view). In particular. FIGS. 10 and 11(a) show the immobilization of the hand (dorsal and palmar views, respectively) on the handboard, with the extended composite sheet 13 in arrangement for electromyographic (EMG) monitoring using a pair of stimulating skin electrodes 14 and recording skin electrodes 15 and ground electrode 32. It is noted that the non-extended composite sheet, as shown in FIGS. 3(a) and 3(b). may also be used for this purpose.

Figure 11C:
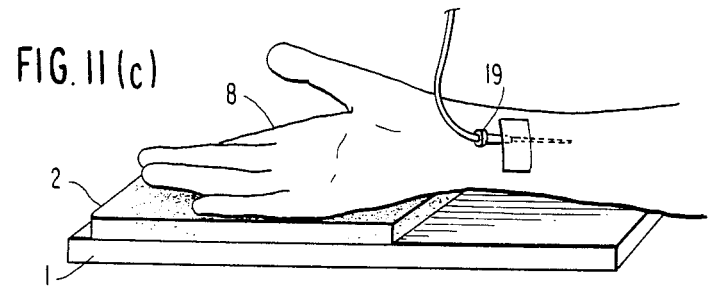

Moreover, the extended composite sheet may be employed in monitoring with an acceleration transducer as shown in FIG. 11(b). The hand is immobilized upon attachment of the extended composite sheet to the hand and armboard Monitoring is accomplished through the employment of stimulating electrodes 16 and an acceleration transducer 17 placed on the thumb 18. FIG. 11(c) further shows the extended composite sheet employed for placement of an intra-arterial blood pressure cannula 19. The intra-arterial blood pressure tubing 30 is attached to adhesive element 6 of the composite sheet 2.

Figure 12:
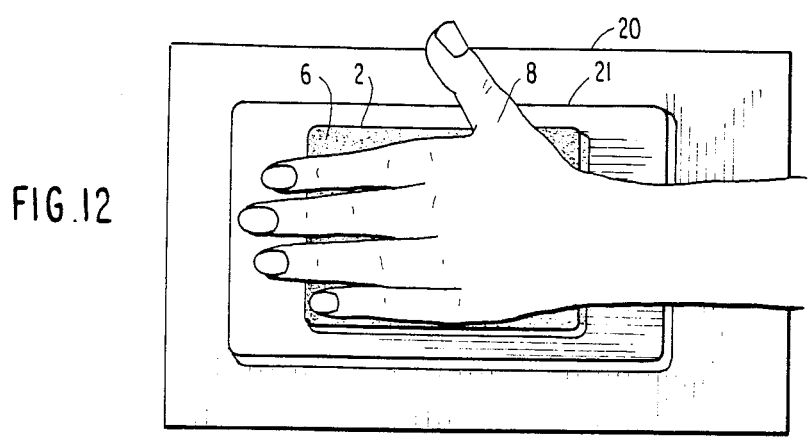
FIG. 12 is a plan view showing the immobilization of the patient's hand through the use of the composite sheet without the armboard according to still a further embodiment of the invention.

A still further embodiment of the present invention allows the hand to be immobilized without the use of an armboard, through the attachment of the composite sheet to the hand. As can be seen from FIG. 12, the hand 8 may be immobilized on any surface 20 with the composite sheet 2 attached to the palm or the back of the hand via the adhesive element 6 and interfacing with the fabric hook fastener 21. The fabric loop fastener (not shown) on the composite sheet 2 forms a loop/hook connection with the fabric hook fastener 21 which is attached to the surface 20, thus forming a hand and/or forearm restraining device without the employment of an armboard. The surface 20 can be any applicable material which is practical and approved for use in hospitals and other health care facilities, operating rooms, recovery rooms and intensive care units. The fabric hook fastener 21 may be permanently attached to the surface 20 by various known means dependent upon the type of material constituting the surface 20.

Figure 13:
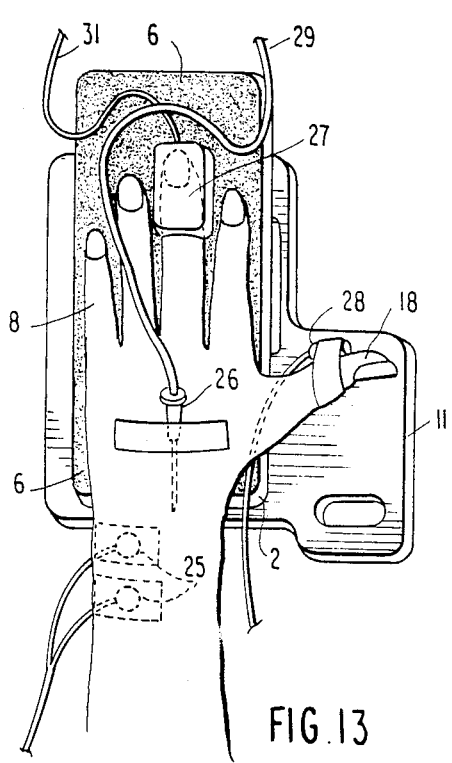
FIGS. 13 and 14 are plan views showing the use of the board and fastening system of the present invention with multiple clinical monitoring devices.
Figure 14:
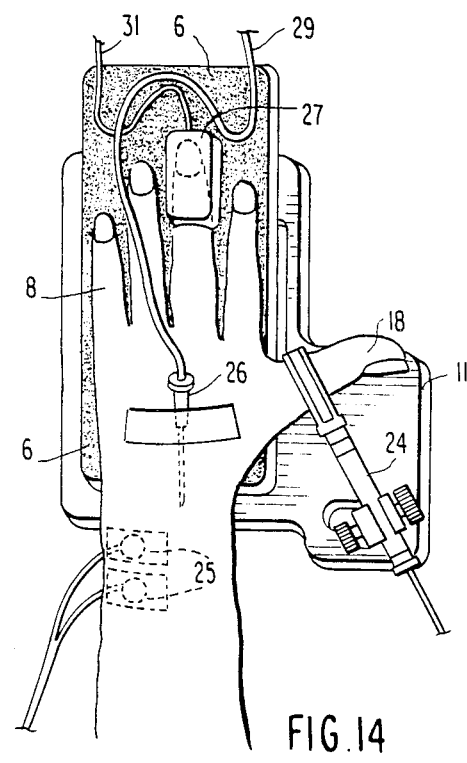

FIGS. 13 and 14 show the simultaneous use of the handboard for multiple purposes. The handboard 1 and the hand 8 with the composite sheet 2 in place, form a secure, reproducible system for immobilization of the hand 8 intravenous tubing 29, oximeter sensor 27 and oximeter sensor cable 31. The composite sheet 2 is attached to the hand B via the adhesive element, as described above. The fabric loop fastener (not shown), which is bound to the opposite side of the composite sheet 8, forms a loop/hook connection with the fabric hook fastener (as in FIG. 6) bound to the handboard 11. This leaves the thumb 18 free to be connected to the acceleration transducer 28 as in FIG. 13, or force transducer 24 as in FIG. 14. The acceleration or force of the thumb 18 is in response to stimulation of the ulnar nerve by a pair of stimulating electrodes 25. Moreover, an IV cannula 26 may be connected to the back of the hand B and IV tubing 29 may be attached to the adhesive component 64. A pulse oximeter sensor 27 may be employed on the patient's finger. The finger with the oximeter sensor 27 in place is immobilized on the adhesive element 6. This stabilizes the oximeter sensor readings by immobilizing both the oximeter sensor 27 and the oximeter sensor cable 31 on the adhesive element 6 during motion. Thus, it prevents erroneous readings during motion. The use of the adhesive element 6 also assures stability of the IV tubing and prevents accidental dislodgement of the IV line by pulling on the IV tubing.

The pressure sensitive adhesive element employed in the present invention is approved for contact With the skin. The size, thickness, and density of the composite sheet may vary according to the specific application of the present invention.

The fabric loop/hook fastening system may be comprised of any such material known in the art. However, a VELCRO fastening system (Tradename of VELCRO USA) is preferred as the fabric loop/hook fastening system for use in the present invention.

The armboard employable in the present invention is shown in the figures as being of a straight, rectangular shape. Such a shape is primarily designed and particularly useful for routine intravenous fluid or blood administration. However, a specific application of the present invention may require a wedged or contoured design of the armboard, in order to accommodate secure and reproducible immobilization of the hand and/or forearm.

The armboard is preferably comprised of a one-piece, lightweight plastic material. However, the choice of material used to produce the armboard is based upon the elasticity or rigidity required according to the specific application of the present invention, and hence, may vary accordingly.

Likewise, the size of the armboard can vary in order to allow for use with all age groups. Furthermore, the handboard may be specifically sized to restrain only the hand of a patient.

While the present invention is particularly useful as a means for securing a patient's hand and/or forearm during intravenous fluid or blood administration the present invention can be used with a variety of clinical monitoring tests and devices.

Thus, it is apparent that the present invention provides a device, and a method for using the same, for immobilizing a patient's hand during intravenous administration of fluids, such as blood, plasma, etc., and to facilitate conducting various monitoring tests. While the invention has been described in accordance with the specific embodiments thereof, it is to be understood that various changes substitutions and alterations can be made without departing from the spirit and the scope of the invention as defined by the claims.

What is claimed is:

1. A restraining device for immobilizing a patient's hand, comprising:
   a rigid member;
   a composite sheet having a pressure sensitive adhesive surface on one side thereof for contact with and adhesive attachment of said hand thereto thereby releasably immobilizing said hand;
   releasable fastening means connected to said rigid member and said composite sheet for fastening said composite sheet to said rigid member, wherein said rigid member, said releasable fastening means, and said composite sheet having said adhesive surface together form a multilayer releasable assembly with said hand adapted to be adhered to said composite sheet.

2. The restraining device as claimed in claim 1, wherein said releasable fastening means comprises:
   a fabric hook fastener bound to at least one side of said rigid member; and
   a fabric loop fastener bound to another side of said composite sheet opposite said one side having said adhesive surface to which said hand is attachable, wherein said hook fastener is fastenable to said loop fastener.

3. The restraining device as claimed in claim 2, further comprising a handbelt fastenable to said rigid member, said handbelt being wrappable around said hand for further immobilization thereof.

4. The restraining device according to claim 3, wherein said handbelt comprises a fabric hook fastener and a fabric loop fastener on opposing ends thereof wherein said said handbelt is connected to said rigid member by fastening said loop fastener of said handbelt to said hook fastener on a side of said rigid member opposite said composite sheet.

5. The restraining device according to claim 4, wherein said rigid member includes an opening through which said handbelt may pass when said handbelt is wrapped around said hand.

6. The restraining device according to claim 4, wherein said handbelt is fastened by fastening said hook fastener and said loop fastener thereof to each other.

7. The restraining device as claimed in claim 1, wherein said composite sheet includes a foam base having said adhesive surface on said one side thereof.

8. The restraining device as claimed in claim 1, wherein said composite sheet is extendable over the fingers of said hand to thereby further immobilize said hand and secure intravenous tubing, intra-arterial blood pressure tubing, oximeter sensor cable and electrode leads connected to the patient.

9. The restraining device according to claim 1, wherein said rigid member has at least one opening for receiving at least one clinical monitoring device.

10. A restraining device for immobilizing a patient's hand by attaching said hand to a rigid surface, comprising: a rigid surface
   a composite sheet having a pressure sensitive adhesive surface on one side thereof for contact with and adhesive attachment of said hand thereto thereby releasably immobilizing said hand; and releasable fastening means connected to said composite sheet for fastening said composite sheet to said rigid surface, wherein said rigid surface, said releasable fastening means, and said composite sheet having said adhesive surface together form a multilayer releasable assembly with said hand adapted to be adhered to said composite sheet.

11. The restraining device according to claim 10, wherein said releasable fastening means comprises:

a fabric loop fastener bound to another side of said composite sheet opposite said one side having said adhesive surface to which said hand is attachable, wherein said loop fastener can be attached to said rigid surface.

12. The restraining device according to claim 10, wherein said fastening means comprises:

an adhesive layer disposed on another side of said composite sheet opposite said side to which said hand is attachable, wherein said adhesive layer is adhesively attachable to said rigid surface.

13. A method for immobilizing a patient's hand with a restraining device which includes a rigid member having a fabric hook fastener on a side thereof and a composite sheet having an adhesive surface on one side and a fabric loop fastener on an opposing side thereof, comprising the steps of:

placing said hand on said adhesive side of said composite sheet.

attaching said hook fastener of said rigid member to said loop faster of said composite sheet to thereby attach said hand to said rigid member.

* * * * *